US007186555B1

(12) United States Patent
Tracey et al.

(10) Patent No.: US 7,186,555 B1
(45) Date of Patent: Mar. 6, 2007

(54) PREVENTION OF BRAIN DAMAGE IN STROKE

(75) Inventors: Kevin J. Tracey, Old Greenwich, CT (US); Haichao Wang, Edison, NJ (US)

(73) Assignee: The Feinstein Institute for Medical Research, Manhasset, NY (US)

( * ) Notice: Subject to any disclaimer, the term of this patent is extended or adjusted under 35 U.S.C. 154(b) by 0 days.

(21) Appl. No.: 09/958,585

(22) PCT Filed: Apr. 13, 2000

(86) PCT No.: PCT/US00/10002

§ 371 (c)(1),
(2), (4) Date: Mar. 27, 2002

(87) PCT Pub. No.: WO00/60943

PCT Pub. Date: Oct. 19, 2000

Related U.S. Application Data

(60) Provisional application No. 60/129,288, filed on Apr. 13, 1999.

(51) Int. Cl.
*C12N 5/00* (2006.01)
(52) U.S. Cl. ............... 435/374; 435/1.1; 435/325; 514/8
(58) Field of Classification Search ............ 435/325, 435/374, 1.1; 514/8
See application file for complete search history.

(56) References Cited

U.S. PATENT DOCUMENTS

| 6,011,005 A * | 1/2000 | Tracey et al. ............ 514/2 |
| 6,051,401 A * | 4/2000 | Chan et al. ............ 435/69.1 |
| 6,117,837 A * | 9/2000 | Tracey et al. ............ 514/2 |
| 6,319,894 B1 * | 11/2001 | Tracey et al. ............ 514/8 |

OTHER PUBLICATIONS

Elzanowski et al., Cystatin Domains in Alpha-2-HS-Glycoprotein and Fetuin. FEBS Letters, 227(2):167-70, Jan. 25, 1988.
Hayase et al., Comparison of N-Glycosides of Fetuins from Different Species and Human Alpha 2-HS-Glycoprotein. Biochemistry, 31(20):4915-21, May 26, 1992.
Lee et al., Human Alpha 2-HS-Glycoprotein: The A and B Chains with a Connecting Sequence are Encoded by a Single mRNA Transcript. Proc. Nat. Acad. Sci U.S.A., 84(13):4403-7, Jul. 1987.
Osawa et al., Haplotype and Analysis of the Human Alpha 2-HS Glycoprotein (Fetuiin) Gene. Ann Hum Genetics, 65(1):27-34, Jan. 2001.
Osawa et al., Structure of the Gene Encoding Human Alpha 2-HS Glycoprotein (AHSG). Gene, 196(1-2):121-25, Sep. 1, 1997.
Rauth et al., The Nucleotide and Partial Amino Acid Sequences of Rat Fetuin. Identify with the Natural Tyrosine Kinase Inhibitor of the Rat Insulin Receptor. Eur. J. Biochemstry, 204(2):523-29, Mar. 1992.
Saunders et al., Expression and Distribution of Fetuin in the Developing Sheep Fetus. Histochemistry, 102(6):457-75, Dec. 1994.
Yang et al., Human Alpha 2-HS-Glycoprotein/Bovine Fetuin Homologue in Mice: Identification and Developmental Regulation of the Gene. Biochim. Biophys. Acta., 1130(2):149-56, Mar. 24, 1992.
Brown et al., Fetuin-An Old Friend Revisited. Bioessays, 14(11):749-55, Nov. 1992.
Brown et al., The Nucleotide and Deduced Amino Acid Structures of Sheep and Pig Fetuin. Common Structural Features of the Mammalian Fetuin Family. Eur. J. Biochem., 205(1):321-31, Apr. 1, 1992.
Brown et al., The Rat Protein Encoded by Clone pp63 is a Fetuin/Alpha 2-HS Glycoprotein-Like Molecule, but is it the Tyrosine Kinase Inhibitor pp63? Cell, 68(1):7-8, Jan. 10, 1992.
Christie et al., Fetuin: The Bovine Homologue of Human Alpha 2HS Glycoprotein. FEBS Letters, 214(1):45-49, Apr. 6, 1987.
Dzeigielewska et al., The Expression of Fetuin in the Development and Maturation of the Hemopoietic and Immune Systems. Histochem Cell Biology, 106(3):319-30, Sep. 1996.
Dziegielewska et al, Alpha 2HS-Glycoprotein is Expressed at High Concentration in Human Fetal Plasma and Cerebrospinal Fluid. Fetal Diagn. Ther., 8(1):22-27, Jan.-Feb. 1993.
Dzeigielewska et al., Fetuin: An Acute Phase Protein in Cattle, J Comp Physiol B, 162(2):168-71, 1992.
Dzeigielewska et al., Fetuin: A New Acute Phase Protein in the Adult and in the Fetus, Folia Histochem Cytobiol, 30(4):187-90, 1992.
Dziegielewska et al, A Fetuin-Related Glycoprotein (Alpha 2HS) in Human Embryonic and Fetal Development, Cell Tissue Research, 248(1):33-41, Apr. 1987.
Dziegielewska et al, The Complete cDNA and Amino Acid Sequence of Bovine Fetuin. Its Homology with Alpha 2HS Glycoprotein and Relation to Other Members of the Cystatin Superfamily. J. Biological Chemistry, 265(8):4354-57, Mar. 15, 1990.
Jahnen-Dechent et al., Postranslational Processing of Human Alpha 2-HS Glycoprotein (Human Fetuin). Evidence for the Production of a Phosphorylated Single-Chain Form by Hepatoma Cells. Eur. J. Biochmistry, 226(1):59-69, Nov. 15, 1994.

\* cited by examiner

*Primary Examiner*—Leon Blaine Lankford, Jr.
(74) *Attorney, Agent, or Firm*—Amster Rothstein & Ebenstein LLP

(57) ABSTRACT

The present invention provides methods and pharmaceutical compositions of the human glycoprotein fetuin, or α2-HS glycoprotein, or fragments thereof to mitigate tissue damage associated with ischemia, particularly in stroke or in myocardial infarction.

6 Claims, 4 Drawing Sheets

Fig.1A.
Fig.1B.
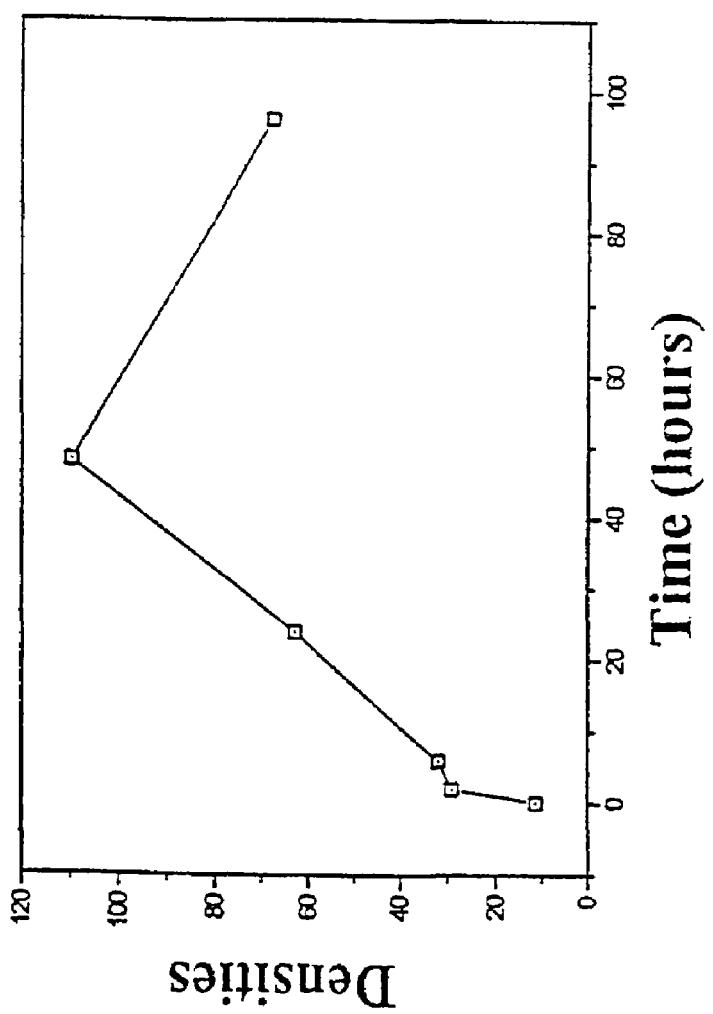
FIGURE 1

SEQUENCE LISTING

```
<160> NUMBER OF SEQ ID NOS: 6

<210> SEQ ID NO 1
<211> LENGTH: 367
<212> TYPE: PRT
<213> ORGANISM: Homo sapiens

<400> SEQUENCE: 1

Met Lys Ser Leu Val Leu Leu Leu Cys Leu Ala Gln Leu Trp Gly Cys
1               5                   10                  15

His Ser Ala Pro His Gly Pro Gly Leu Ile Tyr Arg Gln Pro Asn Cys
            20                  25                  30

Asp Asp Pro Glu Thr Glu Glu Ala Ala Leu Val Ala Ile Asp Tyr Ile
        35                  40                  45

Asn Gln Asn Leu Pro Trp Gly Tyr Lys His Thr Leu Asn Gln Ile Asp
    50                  55                  60

Glu Val Lys Val Trp Pro Gln Gln Pro Ser Gly Glu Leu Phe Glu Ile
65                  70                  75                  80
```

-continued

```
Glu Ile Asp Thr Leu Glu Thr Cys His Val Leu Asp Pro Thr Pro
                85                  90                  95

Val Ala Arg Cys Ser Val Arg Gln Leu Lys Glu His Ala Val Glu Gly
            100                 105                 110

Asp Cys Asp Phe Gln Leu Leu Lys Leu Asp Gly Lys Phe Ser Val Val
        115                 120                 125

Tyr Ala Lys Cys Asp Ser Ser Pro Asp Ser Ala Glu Asp Val Arg Lys
    130                 135                 140

Val Cys Gln Asp Cys Pro Leu Leu Ala Pro Leu Asn Asp Thr Arg Val
145                 150                 155                 160

Val His Ala Ala Lys Ala Ala Leu Ala Ala Phe Asn Ala Gln Asn Asn
                165                 170                 175

Gly Ser Asn Phe Gln Leu Glu Glu Ile Ser Arg Ala Gln Leu Val Pro
            180                 185                 190

Leu Pro Pro Ser Thr Tyr Val Glu Phe Thr Val Ser Gly Thr Asp Cys
        195                 200                 205

Val Ala Lys Glu Ala Thr Glu Ala Ala Lys Cys Asn Leu Leu Ala Glu
    210                 215                 220

Lys Gln Tyr Gly Phe Cys Lys Ala Thr Leu Ser Glu Lys Leu Gly Gly
225                 230                 235                 240

Ala Glu Val Ala Val Thr Cys Thr Val Phe Gln Thr Gln Pro Val Thr
                245                 250                 255

Ser Gln Pro Gln Pro Glu Gly Ala Asn Glu Ala Val Pro Thr Pro Val
            260                 265                 270

Val Asp Pro Asp Ala Pro Pro Ser Pro Pro Leu Gly Ala Pro Gly Leu
        275                 280                 285

Pro Pro Ala Gly Ser Pro Pro Asp Ser His Val Leu Leu Ala Ala Pro
    290                 295                 300

Pro Gly His Gln Leu His Arg Ala His Tyr Asp Leu Arg His Thr Phe
305                 310                 315                 320

Met Gly Val Val Ser Leu Gly Ser Pro Ser Gly Glu Val Ser His Pro
                325                 330                 335

Arg Lys Thr Arg Thr Val Val Gln Pro Ser Val Gly Ala Ala Ala Gly
            340                 345                 350

Pro Val Val Pro Pro Cys Pro Gly Arg Ile Arg His Phe Lys Val
        355                 360                 365
```

<210> SEQ ID NO 2
<211> LENGTH: 16
<212> TYPE: PRT
<213> ORGANISM: Homo sapiens

<400> SEQUENCE: 2

```
Met Lys Ser Leu Val Leu Leu Leu Cys Leu Ala Gln Leu Trp Gly Cys
1               5                   10                  15
```

<210> SEQ ID NO 3
<211> LENGTH: 282
<212> TYPE: PRT
<213> ORGANISM: Homo sapiens

<400> SEQUENCE: 3

```
Ala Pro His Gly Pro Gly Leu Ile Tyr Arg Gln Pro Asn Cys Asp Asp
1               5                   10                  15

Pro Glu Thr Glu Glu Ala Ala Leu Val Ala Ile Asp Tyr Ile Asn Gln
            20                  25                  30
```

```
Asn Leu Pro Trp Gly Tyr Lys His Thr Leu Asn Gln Ile Asp Glu Val
            35                  40                  45
Lys Val Trp Pro Gln Gln Pro Ser Gly Glu Leu Phe Glu Ile Glu Ile
 50                  55                  60
Asp Thr Leu Glu Thr Thr Cys His Val Leu Asp Pro Thr Pro Val Ala
 65                  70                  75                  80
Arg Cys Ser Val Arg Gln Leu Lys Glu His Ala Val Glu Gly Asp Cys
                 85                  90                  95
Asp Phe Gln Leu Leu Lys Leu Asp Gly Lys Phe Ser Val Val Tyr Ala
                100                 105                 110
Lys Cys Asp Ser Ser Pro Asp Ser Ala Glu Asp Val Arg Lys Val Cys
                115                 120                 125
Gln Asp Cys Pro Leu Leu Ala Pro Leu Asn Asp Thr Arg Val Val His
                130                 135                 140
Ala Ala Lys Ala Ala Leu Ala Ala Phe Asn Ala Gln Asn Asn Gly Ser
145                 150                 155                 160
Asn Phe Gln Leu Glu Glu Ile Ser Arg Ala Gln Leu Val Pro Leu Pro
                165                 170                 175
Pro Ser Thr Tyr Val Glu Phe Thr Val Ser Gly Thr Asp Cys Val Ala
                180                 185                 190
Lys Glu Ala Thr Glu Ala Ala Lys Cys Asn Leu Leu Ala Glu Lys Gln
                195                 200                 205
Tyr Gly Phe Cys Lys Ala Thr Leu Ser Glu Lys Leu Gly Gly Ala Glu
                210                 215                 220
Val Ala Val Thr Cys Thr Val Phe Gln Thr Gln Pro Val Thr Ser Gln
225                 230                 235                 240
Pro Gln Pro Glu Gly Ala Asn Glu Ala Val Pro Thr Pro Val Val Asp
                245                 250                 255
Pro Asp Ala Pro Pro Ser Pro Leu Gly Ala Pro Gly Leu Pro Pro
                260                 265                 270
Ala Gly Ser Pro Pro Asp Ser His Val Leu
                275                 280
```

<210> SEQ ID NO 4
<211> LENGTH: 27
<212> TYPE: PRT
<213> ORGANISM: Homo sapiens

<400> SEQUENCE: 4

```
Thr Val Val Gln Pro Ser Val Gly Ala Ala Gly Pro Val Val Pro
 1                   5                  10                  15
Pro Cys Pro Gly Arg Ile Arg His Phe Lys Val
                 20                  25
```

<210> SEQ ID NO 5
<211> LENGTH: 40
<212> TYPE: PRT
<213> ORGANISM: Homo sapiens

<400> SEQUENCE: 5

```
Leu Ala Ala Pro Pro Gly His Gln Leu His Arg Ala His Tyr Asp Leu
 1                   5                  10                  15
Arg His Thr Phe Met Gly Val Val Ser Leu Gly Ser Pro Ser Gly Glu
                 20                  25                  30
Val Ser His Pro Arg Lys Thr Arg
                 35                  40
```

```
<210> SEQ ID NO 6
<211> LENGTH: 341
<212> TYPE: PRT
<213> ORGANISM: Bos taurus

<400> SEQUENCE: 6

Ile Pro Leu Asp Pro Val Ala Gly Tyr Lys Glu Pro Ala Cys Asp Asp
 1               5                  10                  15

Pro Asp Thr Glu Gln Ala Ala Leu Ala Ala Val Asp Tyr Ile Asn Lys
            20                  25                  30

His Leu Pro Arg Gly Tyr Lys His Tyr Leu Asn Gln Ile Asp Ser Val
         35                  40                  45

Lys Val Trp Pro Arg Arg Pro Thr Gly Glu Val Tyr Asp Ile Glu Ile
     50                  55                  60

Asp Thr Leu Glu Thr Thr Cys His Val Leu Asp Pro Thr Pro Leu Ala
 65                  70                  75                  80

Asn Cys Ser Val Arg Gln Gln Thr Gln His Ala Val Glu Gly Asp Cys
                 85                  90                  95

Asp Ile His Val Leu Lys Gln Asp Gly Gln Phe Ser Val Leu Phe Thr
            100                 105                 110

Lys Cys Asp Ser Ser Pro Asp Ser Ala Glu Asp Val Arg Lys Leu Cys
        115                 120                 125

Pro Asp Cys Pro Leu Leu Ala Pro Leu Asn Asp Ser Arg Val Val His
    130                 135                 140

Ala Val Glu Val Ala Leu Ala Thr Phe Asn Ala Glu Ser Asn Gly Ser
145                 150                 155                 160

Tyr Leu Gln Leu Val Glu Ile Ser Arg Ala Gln Phe Val Pro Leu Pro
                165                 170                 175

Val Ser Val Ser Val Glu Phe Ala Val Ala Ala Thr Asp Cys Ile Ala
            180                 185                 190

Lys Glu Val Val Asp Pro Thr Lys Cys Asn Leu Leu Ala Glu Lys Gln
        195                 200                 205

Tyr Gly Phe Cys Lys Gly Ser Val Ile Gln Lys Ala Leu Gly Gly Glu
    210                 215                 220

Asp Val Arg Val Thr Cys Thr Leu Phe Gln Thr Gln Pro Val Ile Pro
225                 230                 235                 240

Gln Pro Gln Pro Asp Gly Ala Glu Ala Glu Ala Pro Ser Ala Val Pro
                245                 250                 255

Asp Ala Ala Gly Pro Thr Pro Ser Ala Ala Gly Pro Pro Val Ala Ser
            260                 265                 270

Val Val Val Gly Pro Ser Val Val Ala Val Pro Leu Pro Leu His Arg
        275                 280                 285

Ala His Tyr Asp Leu Arg His Thr Phe Ser Gly Val Ala Ser Val Glu
    290                 295                 300

Ser Ser Ser Gly Glu Ala Phe His Val Gly Lys Thr Pro Ile Val Gly
305                 310                 315                 320

Gln Pro Ser Ile Pro Gly Gly Pro Val Arg Leu Cys Pro Gly Arg Ile
                325                 330                 335

Arg Tyr Phe Lys Ile
            340
```

PREVENTION OF BRAIN DAMAGE IN STROKE

CROSS-REFERENCE TO RELATED APPLICATIONS

This application is a U.S. national phase filing of PCT Application No. PCT/US00/10002, filed on Apr. 13, 2000, and claims the benefit of U.S. Provisional Application No. 60/129,288, filed on Apr. 13, 1999.

TECHNICAL FIELD OF THE INVENTION

The present invention provides a method and a pharmaceutical composition useful to mitigate tissue damage associated with ischemia, particularly of the brain (stroke, brain attack) and heart (myocardial infarction, heart attack).

BACKGROUND OF THE INVENTION

Cerebral ischemia, also termed "stroke" or "brain attack," is a leading cause of mortality and neurologic disability worldwide, but proven treatment options are severely limited. Recent clinical results indicate that the timely administration of thrombolytic agents can improve the outcome from stroke by restoring blood flow to the ischemic brain, for instance, but this approach has its limitations and additional therapeutic modalities are urgently needed (Anonymous, *N Engl J Med* 333:1581–1587, 1995). The timing of therapeutic intervention against stroke damage is critical because outside the most profoundly ischemic zone where all cells are destined to die (the "ischemic core"), lies a "penumbral zone" where brain cell death slowly continues to occur for minutes, hours and days after the onset of ischemia. Delayed cell death in the under-perfused penumbral region is caused by a poorly understood cascade of cytotoxic mediators that kill otherwise potentially viable cells. The time course of progressive brain damage within this penumbra limits the duration of the therapeutic window, and new therapeutic approaches will depend first on the identification of responsible cytotoxic mediators and secondly on the identification of antagonists that can be administered within the therapeutic window. Thus the goal of therapy for cerebral infarction is to prevent the loss of potentially viable brain tissue in the early hours after the onset of ischemia, and there is a need to identify both target mechanisms of cytotoxicity and suitable antagonist agents to minimize brain damage in stroke.

alpha-2HS-Glycoprotein (α2-HS), sometimes called human fetuin, is the human homolog of the bovine protein originally isolated as fetuin. Alpha-2HS-Glycoprotein is a major protein occurring in human blood and calciferous tissues (where has been known as "bone resorptive protein-2," or BRP-2). Due to extensive sequence identity, α2-HS has been grouped with the fetuins, a family of proteins that occur in fetal plasma in high concentrations. Native α2-HS undergoes a series of posttranslational modifications including proteolytic processing, multiple N-glycosylations and O-glycosylations, sulfation of the carbohydrate side chains, and phosphorylation, such that slightly differing mature forms may be present. α2-HS is generally considered to comprise two polypeptide chains, the A chain (282 amino acids) with five internal disulfide bridges forming it into a series of loops, and the B chain (27 amino acids) linked by a single disulfide bridge to the A chain. Human fetuin, or α2-HS, is generally considered to arise from a single mRNA transcript encoding a 367 amino acid peptide known as the "alpha-2-HS-glycoprotein precursor" (SEQ ID NO. 1). Amino acids 1–18 (SEQ ID NO. 2) comprise a signal sequence domain. Amino acids 19–300 comprise the α2-HS-glycoprotein A chain domain (SEQ ID NO. 3). Amino acids 341–367 comprise the α2-HS-glycoprotein B chain domain (SEQ ID NO. 4). By inference, amino acids 301–340 comprise a 40 amino acid connecting sequence (SEQ ID NO. 5) that is not present in the mature form, although single chain forms of α2-HS have been isolated (Jahnen-Dechent et al., *Eur. J Biochem.* 226:59–69, 1994).

Fetuin was first identified more than 50 years ago as a major protein component of bovine fetal serum but its biological function remains unclear, particularly as a circulating protein. Bovine fetuin occurs as a single chain, globular 341 amino acid polypeptide (amino acids 19–359 of the 359 amino acid bovine fetuin precursor) with six internal disulfide bonds and three N-linked and two O-linked oligosaccharides (SEQ ID NO. 6). Primary amino acid sequence and the position of cysteine residues are well conserved across species, e.g., human, bovine, sheep, rat and mouse (Dziegielewska et al., *J. Biol. Chem.* 265:4354, 1990; Rauth et al., *Euro J. Biochem.* 205:321, 1992; Lee et al., *Proc. Natl. Acad. Sci. USA* 84:4403, 1987; and Brown et al., *Eur. J. Biochem.* 205:321, 1992). Fetuin (α2-HS) levels in human plasma are regulated in the manner of a negative acute phase reactant (Lebreton et al., *J. Clin. Invest.* 64:1118, 1979). IL-1 was shown to suppress α2-HS transcript levels in cultured hepatocytes (Akhoundi et al., *J. Biol. Chem.* 268:15925, 1994). α2-HS appears to be expressed in bone because transcripts have been detected in both chondrocytes and osteoblasts (Yang et al., *Blood* 12:7, 1991), and α2-HS influences the mineral phase of bone. The α2-HS glycoprotein is the human homolog of fetuin and is secreted in high levels by adult liver into the peripheral circulation (Triffitt et al., *Nature* 262:226, 1976).

Human fetuin (α2-HS) has 2 N-linked oligosaccharide chains (attached to the amine nitrogen atom of asparagine), and 3 O-linked oligosaccharide chains (attached to the oxygen atom of serine or threonine). The sugar moiety directly attached to the α2-HS polypeptide is usually a N-acetylglucosamine residue. The terminal sugar residue is usually a sialic acid, in particular a N-acetylneuraminic acid (NANA) residue, which bears a net negative charge. If one removes the terminal sialic acid residue from α2-HS by neuraminidase treatment, the resulting glycoprotein is an asialofetuin. Fetuin (α2-HS) is also a carrier protein for growth factors and cytokines. The synthesis of human α2-HS-glycoprotein is down-regulated by cytokines (hIL-1β, hIL-6) (Lebreton et al., *J. Clin. Invest.* 64:1118–1129, 1979). Human fetuin (α2-HS) levels are decreased (25–50%) in trauma patients (van Oss et al., *J. Trauma* 15:451, 1975). α2-HS is structurally related to the cystatins and kininogens.

SUMMARY OF THE INVENTION

"Fetuin" as used herein refers, in the context of the human protein, to the glycoprotein referred to variously as "α2-HS-glycoprotein" or "α2-Z-globulin" or "human fetuin" or "human fetuin glycoprotein," and in broader context to any of the fetuin family of proteins, with members occurring in various species and closely related in sequence to bovine fetuin and human α2-HS. Two common alleles are known for α2-HS: one has threonine at position 248 and 256, the other has methionine at 248 and serine at 256. Use of "fetuin" or "α2-HS" according to the teachings herein shall correspondingly include use of allelic variants, glycosylation, sulfation and phosphorylation variants, reduced and native forms, precursor and proteolytically processed forms, and sequence variants substantially homologous to the polypeptides described by SEQ ID NO.'s 1–6 or to the fetuins of other (non-human) species, and fragments of any of the above. Such variants, whether naturally occurring, intentionally introduced or spontaneously arising, are conveniently tested for activity (and thereby evaluated for clinical utility) in accordance with the Detailed Description and Examples described herein.

The present invention arose out of a series of experiments wherein brain damage (cell death) subsequent to induced focal ischemia was found to be ameliorated by treatment with the glycoprotein α2-HS. The present invention identifies for the first time the cellular and tissue protective effects of administering α2-HS in the setting of ischemia. The present invention further provides methods and pharmaceutical compositions for preventing tissue damage in ischemia, particularly brain damage attendant to stroke or cerebral ischemia, comprising administering an effective amount of an α2-HS glycoprotein. Preferably, the α2-HS glycoprotein is a human α2-HS glycoprotein comprising a primary sequence according to SEQ ID NO. 1 through SEQ ID NO. 5 or a shorter fragment thereof. Highly homologous sequence variants are also useful in this regard, particularly such homologous glycoproteins as have effects quantitatively indistinguishable from α2-HS in the assays described herein. Such variant glycoproteins are conveniently produced according to techniques of molecular biology well-known in the art and are readily compared to human α2-HS glycoprotein in the assays described herein, or in comparable assays for cellular or tissue protection in the setting of ischemia.

The utility of the methods and compositions involving α2-HS glycoproteins as taught herein are directly extended to other instances of tissue ischemia, particularly heart attack or myocardial infarction. Stroke (ischemia and associated tissue damage) is well-known to arise from a variety of distal causes, giving rise to such clinical characterizations as: stroke, cerebral infarction, cerebrovascular accident, thrombotic stroke, embolic stroke, occlusive cerebrovascular lesion, apoplexy (of various types), apoplectic stroke, paralytic stroke, intracranial hemorrhage, hemorrhagic stroke, ruptured aneurysm, post-traumatic stroke, transient ischemic attack, and stroke syndrome. Likewise, heart attack may arise variously, giving rise to such representative clinical characterizations as: cardiac infarction, myocardial infarction (various types), coronary artery occlusion, coronary thrombosis, coronary embolism, periarteritis nodosa, and obliterating endarteritis. Similarly, other organs and tissues may become afflicted by ischemia involving, among other conditions, anemic, pale, white or bland infarction, various embolic disorders including embolic infarction, various thrombotic disorders including thrombotic infarction, hemorrhagic or red infarction, and coagulation necrosis. Any of these conditions of ischemia, and their clinical relations, is amenable to treatment according to the methods and with the pharmaceutical compositions taught herein.

BRIEF DESCRIPTION OF THE DRAWINGS

FIG. 1 demonstrates the expression of α2-HS in infarct regions of brain cortex from rats subjected to experimental focal cerebral ischemia. FIG. 1A is a Western blot showing α2-HS protein expression in regions of infarct induced in the brain cortex of rats subjected to experimental focal ischemia. Lane 1, sampled from normal brain; lane 2, two hours post onset of ischemia; lane 3, six hours post onset of ischemia; lane 4, 24 hours post onset of ischemia; lane 5, 48 hours post onset of ischemia; lane 6, 96 hours post onset of ischemia. FIG. 1B is a plot of scanning densitometric values derived from the Western blots of FIG. 1A plotted against hours post onset of ischemia.

DETAILED DESCRIPTION OF THE INVENTION

Figure 2:
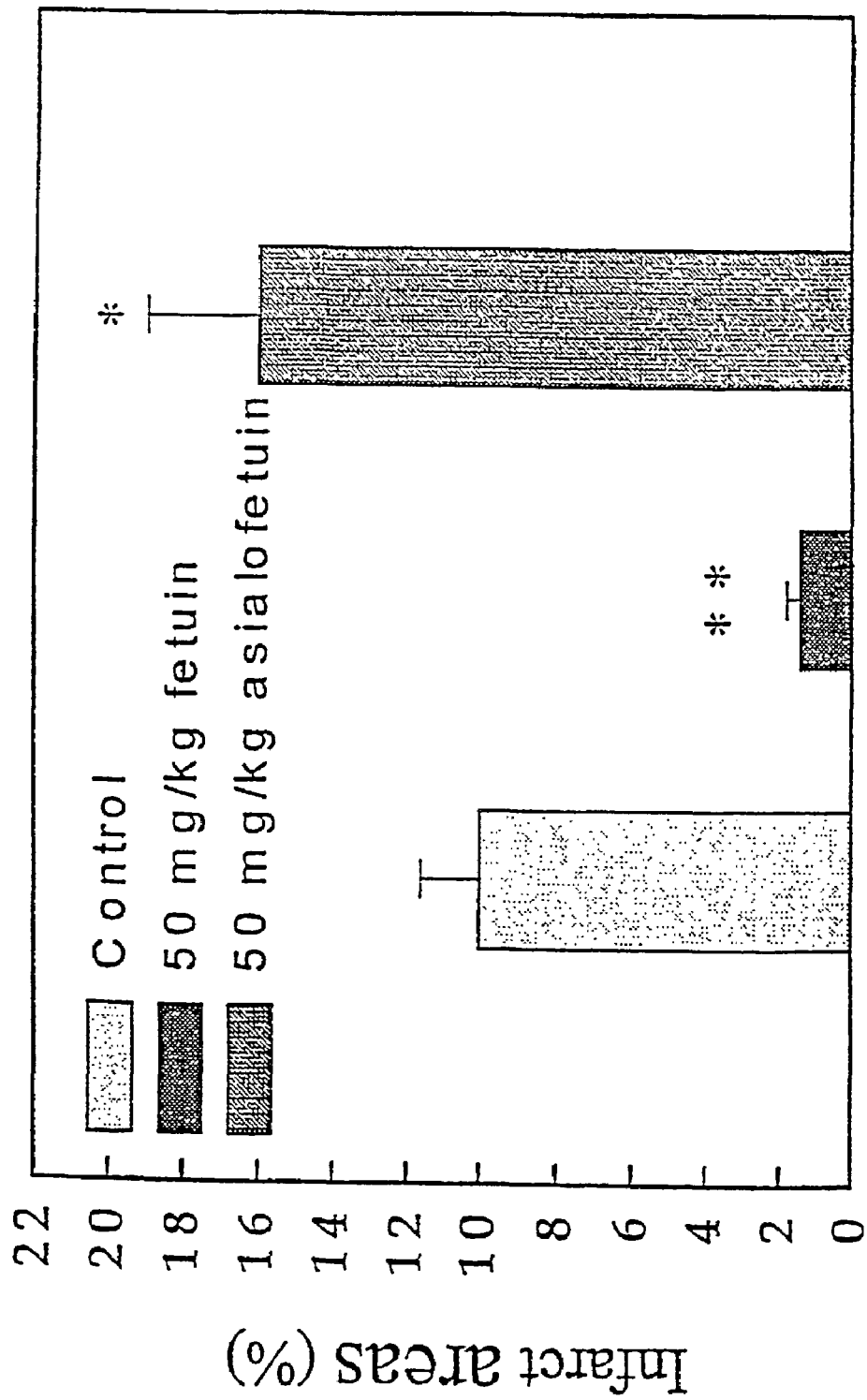
FIG. 2 shows the effects of α2-HS treatment on infarct size in experimental focal cerebral ischemia. α2-HS treatment significantly reduced infarct volume when administered intravenously 15 min after the induction of ischemia. Histograms represent infarct volume as a percentage of half cortical volume 24 hours after onset of ischemia. Asialofetuin worsened brain damage. Values are mean ±SD, n=6; **P<0.01 compared to control and to asialofetuin; *P<0.05 compared to control.

The present invention is based on the discovery that a human plasma glycoprotein, α2-HS, is beneficial in preventing tissue damage associated with ischemia, and specifically in treating stroke. Although fetuin was discovered more than 50 years ago as a component of fetal bovine serum, and subsequently found to share high homology with a human α2-HS counterpart (α2-HS-glycoprotein), no role for α2-HS in the natural history, etiology or treatment of stroke (cerebral infarction, cerebral ischemia, brain attack) or other tissue ischemia had been suspected. After recognizing the activity of α2-HS to potentiate the anti-inflammatory activity of certain low molecular weight compounds and metabolites, we tested for the occurrence and activity of α2-HS in a predictive animal model of human stroke, i.e., in experimentally induced focal cerebral ischemia in rats. We discovered that α2-HS occurs in increasing amounts in the areas of brain damage following permanent focal cerebral ischemia, and that administration of α2-HS alone, even after the onset of ischemia, dose-dependently decreased the volume of total brain damage in stroke. Asialofetuin (α2-HS glycoprotein treated to remove sialic acid residues) was ineffective or exacerbative in this regard.

The present invention provides novel methods (α2-HS administration as adjunctive or monotherapy) and pharmaceutical compositions (comprising α2-HS or glycoprotein sequence variants) to treat and mitigate against tissue damage in ischemia, particularly in stroke and heart attack. Effective doses of the therapy are determined by routine procedures in the art with reference to the findings described herein, and may be formulated in suitable pharmacological carriers for administration by any appropriate means including, but not limited to, injection (such as, intravenous, intramuscular, intrathecal, and intracranial) and other means available within the pharmaceutical arts. Treatment may be accomplished by administration of the α2-HS glycoprotein alone or in a pharmaceutical composition where it is mixed with suitable carriers or excipients to treat tissue ischemia or mitigate against ischemic tissue damage. Preferably, administration of α2-HS is systemic to provide organ sites of treatment including the brain, CNS, myocardium, or other organ site experiencing ischemia. A therapeutically effective dose refers to that amount of the active agent sufficient to treat tissue ischemia or to mitigate against ischemic tissue damage. Therapeutically effective doses may be administered alone or as adjunctive therapy in combination with other treatments or supportive measures for tissue ischemia, particularly for stroke or for heart attack. In particular, α2-HS may be co-administered with spermine or otherwise in accordance with the teachings of U.S. Ser. No. 08/780,311 (filed), the disclosure of which is incorporated herein by reference in its entirety. Techniques for the formulation and administration of the compounds of the instant application may be found in "Remington's Pharmaceutical Sciences," Mack Publishing Company, Easton, Pa., latest edition.

EXAMPLE 1

Appearance of α2-HS in Stroke

We first sought to assess the appearance of α2-HS in ischemic areas of brain, relative to its appearance in the normally perfused brain. A widely used model for human stroke is achieved by permanently occluding the middle cerebral artery in rats, and subsequently measuring the volume of the resultant cortical brain damage after 24 hours. The resulting infarction in this model is highly reproducible and provides a reasonable model of the typical brain damage that occurs in the setting of human focal cerebral ischemia or stroke. Moreover, the clinical efficacy of experimental therapeutics can be conveniently assessed in this model because quantitative volumetric estimates of brain damage can be made, allowing direct comparison between various cerebroprotective strategies and agents. Moreover, therapeutic modalities identified to mitigate against ischemic tissue damage in this model can be directly extended to other tissue ischemias, such as heart attack.

Permanent focal cerebral ischemia: Rats were subjected to a microsurgical right frontal craniotomy and permanent occlusion of the middle cerebral artery as described previously in detail (Zimmerman, et al., *Proc Natl Acad Sci USA*, 92:3744–3748, 1995; Cocroft, et al., *Stroke*, 27:1393–1398, 1996). Briefly, the ipsilateral common carotid artery was ligated and divided, the middle cerebral artery was coagulated and divided distally to the lenticulostriate branch, and the contralateral common carotid artery temporarily occluded (one hour). The onset of ischemia was defined as the time the middle cerebral artery was cut. Twenty-four hours later, the animals were euthanized, fresh brain sections were prepared (1 mm), immersed in a solution of 2,3,5-triphenyl-2H-tetrazolium chloride (2% in 154 mM NaCl) for 30 min at 37° C., and total cerebral infarct volume was estimated by computerized quantitative planimetry. The volume of stroke damage in this model is relatively modest and limited to the cortex such that, behavioral deficits are not readily observable and the animals exhibit normal ambulation, feeding and grooming without seizure or paralysis.

To determine the appearance of α2-HS in normal and in stroke-damaged brain areas, rats were subject to focal cerebral ischemia as above, and brains were collected at various time points after the onset of ischemia. Brain sections corresponding to damaged and normal tissue were isolated and solubilized proteins were analyzed by Western blot using anti-α2-HS antibodies according to well-known protocols. As shown in FIG. 1, immunoreactive α2-HS protein was present in normal brain tissue, and the amount of immunoreactive α2-HS protein increased for up to 48 hours after ischemic insult, with above normal levels persisting for at least 96 hours.

EXAMPLE 2

Effects of α2-HS Treatment on Stroke Damage

Since ischemic brain is known to contain elevated levels of polyamines, and since α2-HS is known to enhance the anti-inflammatory properties of spermine (U.S. Ser. No. 08/932,871, incorporated herein in its entirety), we sought to assess the therapeutic benefit of α2-HS treatment in stroke. As shown in FIG. 2, rats subjected to experimental focal cerebral ischemic challenge suffered smaller infarcts if they were treated intravenously with α2-HS at 50 mg/kg than if they were untreated. Under these conditions, treatment with asialofetuin exacerbated stroke damage. This brain damage-ameliorating effect of α2-HS treatment is predictive of a therapeutic benefit in response to α2-HS treatment in the context of human stroke or cerebrovascular accident, and in other conditions of ischemic tissue damage (e.g., heart attack).

EXAMPLE 3

Inhibition of Brain Damage by α2-HS Treatment is Dose-Dependent

Figure 3:
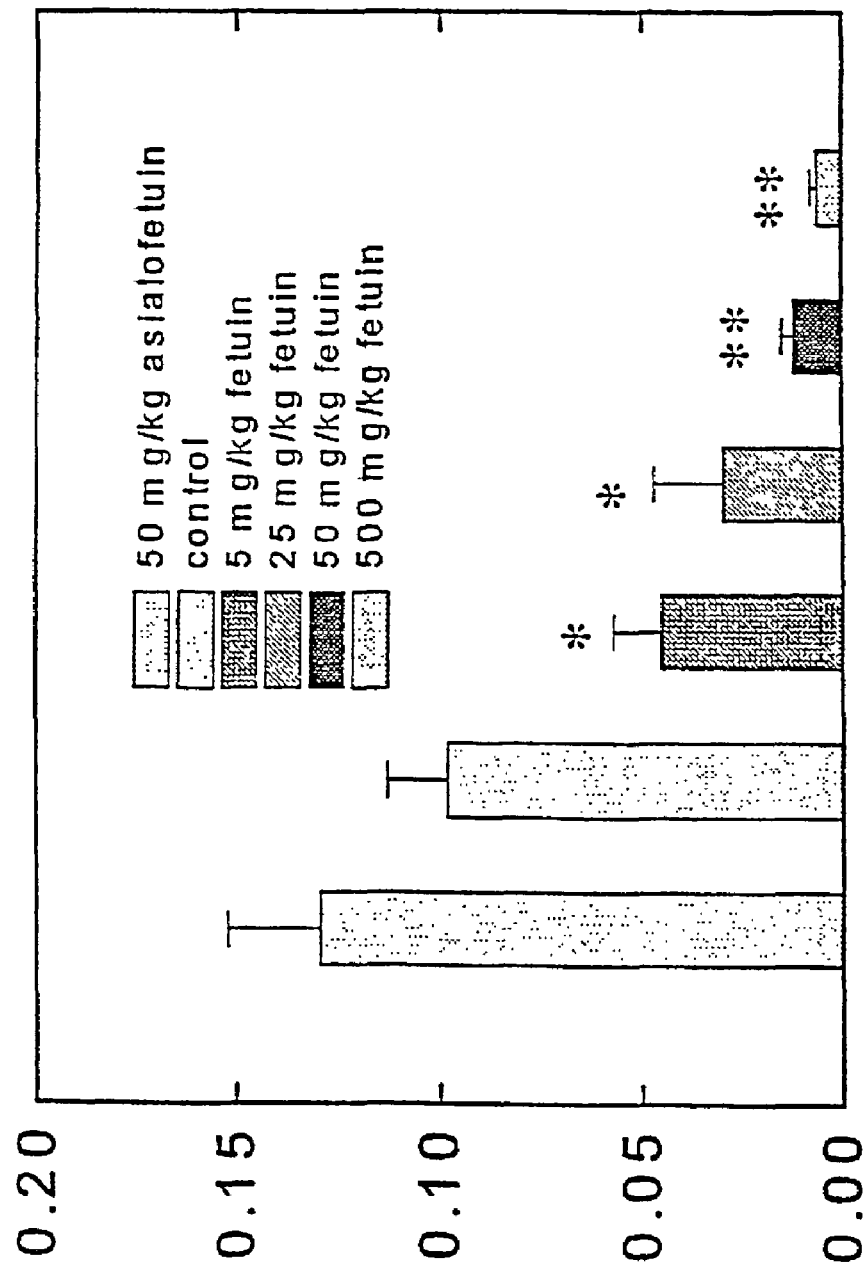
FIG. 3 shows that the therapeutic benefits of α2-HS treatment are dose-dependent. Histograms represent infarct volume as percent of half-cortical volume of brains collected 24 hours after ischemic challenge. Treatments were intravenous 15 minutes after onset of ischemia with from left to right, 50 mg/kg asialofetuin, no treatment control, 5 mg/kg α2-HS, 25 mg/cg α2-HS, 50 mg/kg α2-HS, 500 mg/kg α2-HS. Values represent mean=SD, n=6; **P<0.01 compared to control; *P<0.05 compared to control.

To determine the dose-dependency of α2-HS treatment to prevent tissue damage in the setting of ischemia, we examined various doses of α2-HS for efficacy in a stroke model involving focal cerebral ischemia. Stroke was induced and animals treated as described above, and α2-HS was administered 15 minutes after the onset of ischemia at a dose of 5, 25, 50 or 500 mg/kg. As shown in FIG. 3, α2-HS improved the outcome of stroke at all doses tested, with doses of 50 or 500 mg/kg providing the most significant benefits. This example shows how therapeutically effective dose ranges are initially estimated. Final determination of effective dosages for specific clinical conditions such as stroke or heart attack is readily accomplished by those skilled in the medical and pharmaceutical arts by reference to these pre-clinical results in experimentally induced tissue ischemia.

EXAMPLE 4

Timing of α2-HS Treatment for Stroke

Figure 4:
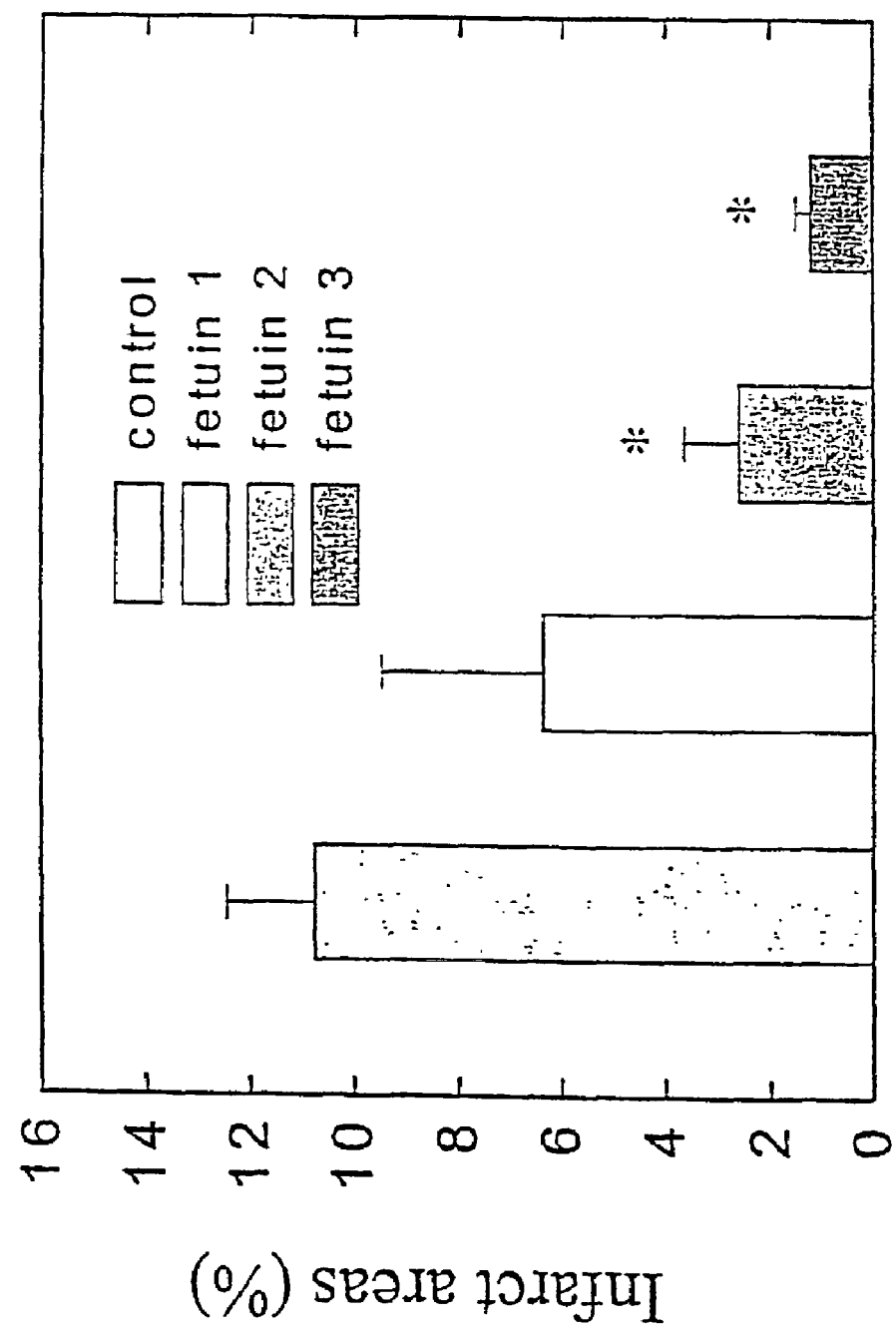
FIG. 4 shows a time course of the therapeutic benefit of α2-HS treatment in stroke. The histograms represent cortical infarct volume as a percentage of half-cortex volume at 24 hours after induction of focal cerebral ischemia in rats. α2-HS was administered at a dose of 50 mg/kg intravenously 60 min α2-HS 1), 30 min (α2-HS 2) or 15 min α2-HS 3) after induction of experimental focal cerebral ischemia in rats. Leftmost bar is control (no α2-HS). Values represent mean±SD, n=6; *P<0.01 compared to control.

We next sought to establish the therapeutic window during which α2-HS treatment would be most beneficial as a treatment for ischemic damage. Rats were subjected to unilateral permanent focal cerebral ischemia and treated intravenously with α2-HS at 50 mg/kg at different latencies after onset of ischemia: 15 minutes, 30 minutes or 60 minutes after permanent occlusion of the middle cerebral artery. As shown in FIG. 4, treatment with α2-HS within 30 minutes following the onset of ischemia was of the greatest benefit in minimizing stroke damage.

In that clinical treatment for stroke (or heart attack or other ischemic conditions) cannot be initiated until after the underlying insult occurs, it is important that α2-HS treatment is of benefit when initiated after the onset of ischemia; this requisite therapeutic window has not always been apparent for other candidate therapeutics against ischemic damage, as some must be initiated before or simultaneously with the onset of ischemia in comparable experimental models. This example shows how the temporal range of therapeutically effective treatment latency is initially estimated. Final determination of the "therapeutic window" during which α2-HS monotherapy or adjunctive therapy is effective for specific clinical conditions such as stroke or heart attack is readily accomplished by those skilled in the medical and pharmaceutical arts, with reference to these pre-clinical results in experimentally induced tissue ischemia.

EXAMPLE 5

Measurement of TNF Levels in the Stroke Model

Brain tissues were fixed by sequential intracardiac perfusion with 0.05 M phosphate buffer saline (PBS, pH 7.4) containing 0.1% sodium nitrate and heparin, followed by infusion with 2% paraformaldehyde in 0.1M PBS (pH 7.4) containing 5% sucrose (for TNF staining), or 4% paraformaldehyde in 0.1M PB (pH 7.4, for α2-HS staining). Following perfusion, the brains were removed and stored in the same fixative solution for 15 min at 4° C. (staining for TNF) and overnight (staining for α2-HS) and then transferred to a solution of 20% sucrose in PBS overnight, at 4° C. The frozen sections of the samples were cut para-sagittally and coronally in alternate series of 20 μm thick with the cryostat. The sections were attached to gelatin-coated slides, air dried, and stored at −20° C. until use. After quenching endogenous peroxidase activity with 0.3% $H_2O_2$ solution, sections were incubated in a 1:20 dilution of either normal horse or goat serum (ACCURATE) for 1 hour. Using an avidin-biotinylated horseradish peroxidase system (DBS), the following were used as primary antibodies for overnight incubation at 4° C. in a humidified chamber. ED1, which is a mouse monoclonal IgG antibody (Accurate Chemical & Scientific Corp.), was used at a dilution of 1:2000; a polyclonal rabbit antimouse TNF-α, (RDI), was used at dilution of 1:100. With intervening washes in PBST, the following steps were performed: biotinylated horse anti-mouse adsorbed (for ED1) and biotinylated goat anti-rabbit (for TNF-α antisera) antibodies (1:150 dilution in PBST) for 1 hour at 25° C.; avidin-biotinylated horseradish peroxidase complex (DBS) in PBST, pH 7.2, for 1 hour at 25° C.; and a 0.1 M solution of 3,3'-diaminobenzidine (DAB) in 0.05 M Tris-HCl buffer, pH 7.4, for 10 min, to which bad been added 0.75 ml of 3% $HO_2$ (for ED1), or 3% 3-amino-9-ethylcarbazole (AEC) in N,N-dimethylformamide (for TNF-α and fetuin), for 15 min.

Administration of α2-HS suppressed TNF production. TNF was not detected in brain sections of normal brain by immunostaining with anti-TNF antibodies. After the onset of cerebral ischemia in the present model, however, TNF immunoreactivity was significantly increased in the ischemic core and penumbra area, but remained undetectable in the contralateral hemisphere. Most TNF-α positive cells in the ipsilateral cortical neuronal layer showed typical morphology of neuronal cells; whereas some TNF-positive cells in the surrounding ventricles, the out most layer of the core, and the corpus collosum in the ischemic hemisphere revealed morphology of microglia cells. Most TNF-positive neronal cells were located in the focal ischemic region (as opposed to the perifocal ischemic area). Treatment of rat with α2-HS at 50 mg/kg 15 minutes after onset of cerebral ischemia significantly decreased TNF immunoreactivity both in the ischemic core and penumbra regions. However, treatment of animals with asialofetuin did not affect the TNF immunoreactivity as compared to controls that treated with control (vehicle) alone, indicating that α2-HS protected against cerebral ischemic injury. Without being bound by theory the mechanism of the therapeutic activity is thought to be at least partially through down-regulation of TNF expression during ischemia.

We claim:

1. A method of treating a subject having tissue ischemia, the method comprising administering human α2-HS glycoprotein to the subject, wherein the human α2-HS glycoprotein comprises the amino acid sequence of
   a) SEQ ID. NO:1, or
   b) both SEQ ID NO: 3 and SEQ ID NO: 4.

2. The method of claim 1 wherein the ischemic tissue is brain or heart.

3. A method of inhibiting tissue damage caused by ischemia in a subject, the method comprising administering to the subject an amount of human α2-HS glycoprotein effective to inhibit the tissue damage, wherein the human α2-HS glycoprotein comprises the amino acid sequence of
   a) SEQ ID. NO:1, or
   b) both SEQ ID NO: 3 and SEQ ID NO: 4.

4. The method of claim 3 wherein the tissue damage is manifest as stroke or myocardial infarction.

5. A method for treating tissue ischemia or preventing ischemic tissue damage in a subject having tissue ischemia, the method comprising administering to the subject a combination of human α2-HS glycoprotein and at least one additional treatment to mitigate ischemic tissue damage, wherein the human α2-HS glycoprotein comprises the amino acid sequence of
   a) SEQ ID. NO:1, or
   b) both SEQ ID NO: 3 and SEQ ID NO: 4.

6. The method of claim 5 wherein the additional treatment to mitigate ischemic tissue damage is an enzymatic clot-dissolving agent.

* * * * *